United States Patent
Wagner et al.

(10) Patent No.: US 6,475,809 B1
(45) Date of Patent: Nov. 5, 2002

(54) PROTEIN ARRAYS FOR HIGH-THROUGHPUT SCREENING

(75) Inventors: Peter Wagner, Cupertino; Dana Ault-Riche; Steffen Nock, both of Palo Alto; Christian Itin, Menlo Park, all of CA (US)

(73) Assignee: Zyomyx, Incorporated, Hayward, CA (US)

( * ) Notice: Subject to any disclaimer, the term of this patent is extended or adjusted under 35 U.S.C. 154(b) by 0 days.

(21) Appl. No.: 09/570,588

(22) Filed: May 12, 2000

Related U.S. Application Data

(62) Division of application No. 09/115,455, filed on Jul. 14, 1998.

(51) Int. Cl.[7] ............................................. G01N 33/543
(52) U.S. Cl. ..................... 436/518; 422/68.1; 435/4; 435/7.1; 436/501; 436/524
(58) Field of Search ..................... 435/4, 7.1; 436/501, 436/518, 524; 422/68.9

(56) References Cited

U.S. PATENT DOCUMENTS

| | | | |
|---|---|---|---|
| 4,071,409 A | | 1/1978 | Messing et al. |
| 4,722,896 A | | 2/1988 | Kadish et al. |
| 4,987,032 A | | 1/1991 | Miyasaka et al. |
| 5,096,807 A | | 3/1992 | Leaback |
| 5,143,854 A | | 9/1992 | Pirrung et al. |
| 5,154,808 A | | 10/1992 | Miyasaka et al. |
| 5,252,743 A | * | 10/1993 | Barrett et al. ............... 548/303 |
| 5,296,114 A | | 3/1994 | Manz |
| 5,304,487 A | | 4/1994 | Wilding et al. |
| 5,405,783 A | | 4/1995 | Pirrung et al. |
| 5,412,087 A | | 5/1995 | Foder et al. |
| 5,441,876 A | | 8/1995 | Singh |
| 5,620,850 A | * | 4/1997 | Bamdad et al. ............. 530/300 |
| 5,624,711 A | * | 4/1997 | Sundberg et al. ........... 427/261 |
| 5,677,196 A | | 10/1997 | Herron et al. |
| 5,726,026 A | | 3/1998 | Wilding et al. |
| 5,766,908 A | | 6/1998 | Klein et al. |
| 5,837,832 A | | 11/1998 | Chee et al. |
| 5,843,767 A | * | 12/1998 | Beattie ....................... 435/287 |
| 5,858,188 A | | 1/1999 | Soane et al. |
| 5,861,242 A | | 1/1999 | Chee et al. |
| 5,866,345 A | | 2/1999 | Wilding et al. |
| 5,919,523 A | * | 7/1999 | Sundberg et al. ........... 427/333 |
| 5,925,552 A | | 7/1999 | Keogh et al. |
| 5,928,880 A | | 7/1999 | Wilding et al. |
| 5,942,443 A | | 8/1999 | Parce et al. |

FOREIGN PATENT DOCUMENTS

| | | |
|---|---|---|
| JP | 02272081 | 11/1990 |
| WO | WO99/40434 | 8/1999 |
| WO | WO00/52209 | 9/2000 |
| WO | WO00/53625 | 9/2000 |
| WO | WO00/54046 | 9/2000 |

OTHER PUBLICATIONS

Nock et al. (1997). Reversible, site specific immobilization of polyarginine–tagged fusion protein on mica surfaces. FEBS Letters. 414:233–238.*

(List continued on next page.)

*Primary Examiner*—Christopher L. Chin
(74) *Attorney, Agent, or Firm*—Alicia J. Hager; Gregory L. Heinkel

(57) ABSTRACT

Protein arrays and protein-coated substrates for the parallel, in vitro screening of biomolecular activity are provided. Methods of using the protein-coated substrates and protein arrays are also disclosed. A plurality of different members of a single protein family may be immobilized on the protein-coated substrate or array. The protein-coated substrates and protein arrays are particularly useful in high-throughput drug screening and clinical diagnostics.

3 Claims, 9 Drawing Sheets

OTHER PUBLICATIONS

Cha et al. Expression of fused protein, human interleukin–2 and green fluorescent protein, in insect larvae. Annual Meeting of The American Institute of Chemical Engineers, Los Angeles, CA, Nov. 1997.*

Memeny. Enzyme–linked immunoassays. In Immuno–Chemistry 1 (eds Johnstone and Turner). p. 147–175, Nov. 1997.*

Mauracher et al. Reduction of rubella ELISA background using heat denatured sample buffer. J. Imminol. Methods. 145:251–254, 1991.*

Colliod et al. "Oriented and covalent immobilization of target molecules to solid supports" Synthesis and application of a light–activatable and thiol–reactive cross–linking reagent *Bioconjugate Chem.* 4:528–536 (1993).

Dzgoev et al "Microformat imaging ELISA for pesticide determination" *Anal. Chem.* 68(19):3364 (1996).

Ekins "Ligand assays" from electrophoresis to miniaturized microarrays *Clin. Chem.* 44(9):2015–2030 (1998).

Elkins et al. "Multianalyte microspote immunoassay–microanalytical compact "compact disk" of the future" Clin. Chem. 37(11):1955–1967 (1991).

Jacobson et al. "Fused quartz substrates for microchip electrophoresis" *Anal. Chem.* 67:2059–2063.

Jones et al. "Microminiaturized immunoassays using atomic force microscopy and compositionally patterned antigen arrays" *Anal. Chem.* 70(7):1223–1241 (1998).

Lemmo et al. "Characterization of inkjet chemical microdispensor for combinatorial library synthesis" Anal. Chem. 69:543–551 (1997).

Kricka "Miniaturization of analytical systems" *Clin. Chem.* 44(9):2008–2014 (1998).

Marks et al. "By–passing immunication–Human antibodies from V–gene libraries displayed on phage" *J. Mol. Biol.* 222:581–597 (1991).

Martynova et al. "Fabricating of plastic microfluid channels by imprinting methods" *Anal. Chem.* 69:4783–47–89 (1997).

Pale–Grosdemange et al. "Formation of self–assembled monolayers by chemisorption of derivatives of oligo(ethylene glycol) of structure HS(CH2)11(OCH2CH2)mOH on gold" *J. Am. Chem. Soc.* 113(1)12–20 (1991).

Rowe et al. "Array biosensor for simultaneous identification of bacterial, viral and protein analytes" *Anal. Chem.* 71(17):3846–3852 (1999).

Sigal et al. "A self–assembled monolayer for the binding and study of histidine–tagged proteins by surface plasmon resonance" *Anal. Chem* 68:490–497 (1996).

Silzel et al. "Mass–sensing, multianalyte microarray immunoassay with imaging detection" *Clin. Chem.* 44(9):2036–2043 (1998).

Steinnicke et al. "Biochemical characteristics of caspases–3, –6, –7, and –8" *J. Biol. Chem.* 272:25719–25723 (1997).

Talanian et al. "Substrate specificities of capsases family proteases" *J. Biol. Chem.* 272:9677–9682 (1997).

Thornberry "Interleukin–1beta converting enzyme" *Meth. Enzymology* 244:615–631 (1994).

Villa et al. "Caspases and caspase inhibitors" *TIBS* 22:388–393 (1997).

Wilson et al. "Structure and mechanism of interleukin–1beta converting enzyme" *Nature* 370:270–275 (1994).

* cited by examiner

B - B:

PROTEIN ARRAYS FOR HIGH-THROUGHPUT SCREENING

This application is a division of Ser. No. 09/115,455, filed Jul. 14, 1998.

BACKGROUND OF THE INVENTION

A vast number of new drug targets are now being identified using a combination of genomics, bioinformatics, genetics, and high-throughput (HTP) biochemistry. Genomics provides information on the genetic composition and the activity of an organism's genes. Bioinformatics uses computer algorithms to recognize and predict structural patterns in DNA and proteins, defining families of related genes and proteins. The information gained from the combination of these approaches is expected to boost the number of drug targets, usually proteins, from the current 500 to over 10,000 in the coming decade.

The number of chemical compounds available for screening as potential drugs is also growing dramatically due to recent advances in combinatorial chemistry, the production of large numbers of organic compounds through rapid parallel and automated synthesis. The compounds produced in the combinatorial libraries being generated will far outnumber those compounds being prepared by traditional, manual means, natural product extracts, or those in the historical compound files of large pharmaceutical companies.

Both the rapid increase of new drug targets and the availability of vast libraries of chemical compounds creates an enormous demand for new technologies which improve the screening process. Current technological approaches which attempt to address this need include multiwell-plate based screening systems, cell-based screening systems, microfluidics-based screening systems, and screening of soluble targets against solid-phase synthesized drug components.

Automated multiwell formats are the best developed high-throughput screening systems. Automated 96-well plate-based screening systems are the most widely used. The current trend in plate based screening systems is to reduce the volume of the reaction wells further, thereby increasing the density of the wells per plate (96-well to 384-, and 1536-well per plate). The reduction in reaction volumes results in increased throughput, dramatically decreased bioreagent costs, and a decrease in the number of plates which need to be managed by automation.

However, although increases in well numbers per plate are desirable for high throughput efficiency, the use of volumes smaller than 1 microliter in the well format generates significant problems with evaporation, dispensing times, protein inactivation, and assay adaptation. Proteins are very sensitive to the physical and chemical properties of the reaction chamber surfaces. Proteins are prone to denaturation at the liquid/solid and liquid/air interfaces. Miniaturization of assays to volumes smaller than 1 microliter increases the surface to volume ratio substantially. (Changing volumes from 1 microliter to 10 nanoliter increases the surface ratio by 460%, leading to increased protein inactivation.) Furthermore, solutions of submicroliter volumes evaporate rapidly, within seconds to a few minutes, when in contact with air. Maintaining microscopic volumes in open systems is therefore very difficult.

Other types of high-throughput assays, such as miniaturized cell-based assays are also being developed. Miniaturized cell-based assays have the potential to generate screening data of superior quality and accuracy, due to their in vivo nature. However, the interaction of drug compounds with proteins other than the desired targets is a serious problem related to this approach which leads to a high rate of false positive results.

Microfluidics-based screening systems that measure in vitro reactions in solution make use of ten to several-hundred micrometer wide channels. Micropumps, electroosmotic flow, integrated valves and mixing devices control liquid movement through the channel network. Microfluidic networks prevent evaporation but, due to the large surface to volume ratio, result in significant protein inactivation. The successful use of microfluidic networks in biomolecule screening remains to be shown.

Drug screening of soluble targets against solid-phase synthesized drug components is intrinsically limited. The surfaces required for solid state organic synthesis are chemically diverse and often cause the inactivation or non-specific binding of proteins, leading to a high rate of false-positive results. Furthermore, the chemical diversity of drug compounds is limited by the combinatorial synthesis approach that is used to generate the compounds at the interface. Another major disadvantage of this approach stems from the limited accessibility of the binding site of the soluble target protein to the immobilized drug candidates.

DNA microarray technology is not immediately transferable to protein screening microdevices. To date, microarrays are exclusively available for nucleic acid hybridization assays ('DNA-chips'). Their underlying chemistry and materials are not readily transferable to protein assays. Nucleic acids withstand temperatures up to 100° C., can be dried and re-hydrated without loss of activity and bound directly to organic adhesion layers absorbed on surfaces such as glass. In contrast, proteins must remain hydrated, kept at ambient temperatures, and are very sensitive to the physical and chemical properties of the support materials. Therefore, maintaining protein activity at the liquid-solid interface requires entirely different immobilization strategies than those used for nucleic acids. Additionally, the proper orientation of the protein at the interface is desirable to ensure accessibility of their active sites with interacting molecules.

In addition to the goal of achieving high-throughput screening of compounds against targets to identify potential drug leads, researchers also need to be able to identify a highly specific lead compound early in the drug discovery process. Analyzing a multitude of members of a protein family or forms of a polymorphic protein in parallel enables quick identification of highly specific lead compounds. Proteins within a structural family share similar binding sites and catalytic mechanisms. Often, a compound that effectively interferes with the activity of one family member also interferes with other members of the same family. Using standard technology to discover such additional interactions requires a tremendous effort in time and costs and as a consequence is simply not done.

However, cross-reactivity of a drug with related proteins can be the cause of low efficacy or even side effects in patients. For instance, AZT, a major treatment for AIDS, blocks not only viral polymerases, but also human polymerases, causing deleterious side effects. Cross-reactivity with closely related proteins is also a problem with nonsteroidal anti-inflammatory drugs (NSAIDs) and aspirin. These drugs inhibit cyclooxygenase-2, an enzyme which promotes pain and inflammation. However, the same drugs also strongly inhibit a related enzyme, cyclooxygenase-1, that is responsible for keeping the stomach lining and kidneys healthy, leading to common side-effects including stomach irritation.

For the foregoing reasons, there is a need for miniaturized protein arrays and for methods for the parallel, in vitro, high-throughput screening of functionally and/or structurally related protein targets against potential drug compounds in a manner that minimizes reagent volumes and protein inactivation problems.

SUMMARY OF THE INVENTION

The present invention is directed to protein arrays, protein-coated substrates, and methods of use thereof that satisfy the need for parallel, in vitro, high-throughput screening of functionally or structurally related protein targets against potential drug compounds in a manner that minimizes reagent volumes and protein inactivation problems.

In one embodiment, the present invention provides for a protein-coated substrate comprising a plurality of patches arranged in discrete, known regions on a substrate, where a protein with a different, known sequence is immobilized on each patch. Furthermore, each of the patches of the protein-coated substrate of the present invention is separated from neighboring patches by from about 50 nm to about 500 μm.

Biosensors, micromachined devices, and medical devices that comprise the protein-coated substrate of the present invention represent other aspects of the invention.

The present invention also provides an array of proteins comprising a plurality of patches arranged in discrete, known regions on a substrate, where a protein with a different, known sequence is immobilized on each patch. Furthermore, each of the patches of the protein-coated substrate of the present invention is separated from neighboring patches by from about 50 nm to about 500 μm.

The protein immobilized on one patch of the array is preferably different from the protein immobilized on a second patch. In an especially preferred embodiment, the protein that is immobilized on one patch of the array is a member of the same protein family as or is otherwise functionally or structurally related to the proteins immobilized on the other patches of the array.

The patches of the array may also optionally further comprise monolayers (on which the proteins of the patches are immobilized).

At least one coating may be formed on the substrate or applied to the substrate of an array of the present invention such that the coating is positioned between the substrate and the monolayer of each patch.

The coating, or the substrate itself if no coating is used, may optionally possess an ultraflat surface with a mean roughness of less than about 5 angstroms for areas of at least 25 μm². This ultraflat surface optionally may be produced by template stripping.

The monolayer of a patch on the array of the present invention may be a mixed monolayer composed of more than one type of molecule.

The patches of an array of the present invention may further comprise an affinity tag that enhances site-specific immobilization of the biological moiety onto the monolayer.

In one embodiment of the invention, an adaptor molecule may also be present to link the affinity tag to the biological moiety on the patches of the array.

In another version of the invention, the affinity tag, biological moiety, and the adaptor (if present) preferably constitute a fusion protein.

The present invention further provides for methods of using the array to screen a plurality of proteins in parallel for their ability to bind or otherwise interact with a component of a fluid sample. Most of these methods involve first delivering the fluid sample to the array. If binding is to be detected, the array may then be optionally washed to remove any unbound component from the area. The methods then involve detecting, either directly or indirectly, the presence or absence of the component retained at each patch or other evidence of an interaction of the protein of a given patch with the component.

Similar methods may be used diagnostically to screen a fluid sample with the array for the presence, absence, or amount of a plurality of analytes at the same time.

The present invention also provides for methods of determining in parallel whether or not a plurality of proteins belongs to a certain protein family. These methods involve delivering a fluid sample comprising a ligand of a known protein family to the patches of the array and then detecting, either directly or indirectly, for the interaction or binding of the known ligand to the patches that would be characteristic the known protein family.

Another aspect of the invention is a protein-coated substrate that comprises a fusion protein immobilized on a monolayer on a portion of the surface of a substrate. The fusion protein is immobilized with the aid of an affinity tag that enhances the site-specific immobilization of the fusion protein onto the monolayer. Here the fusion protein comprises a polypeptide that serves as an adaptor molecule by linking another polypeptide to the affinity tag. The monolayer of the protein-coated substrate comprises molecules of the formula X-R-Y where R is a spacer, X is a functional group that binds R to the surface, and Y is a functional group for binding the fusion protein onto the monolayer. The protein-coated substrate may optionally also include a coating between the substrate and the monolayer and the affinity tag may optionally constitute a part of the fusion protein.

DETAILED DESCRIPTION OF THE INVENTION

Figure 1:
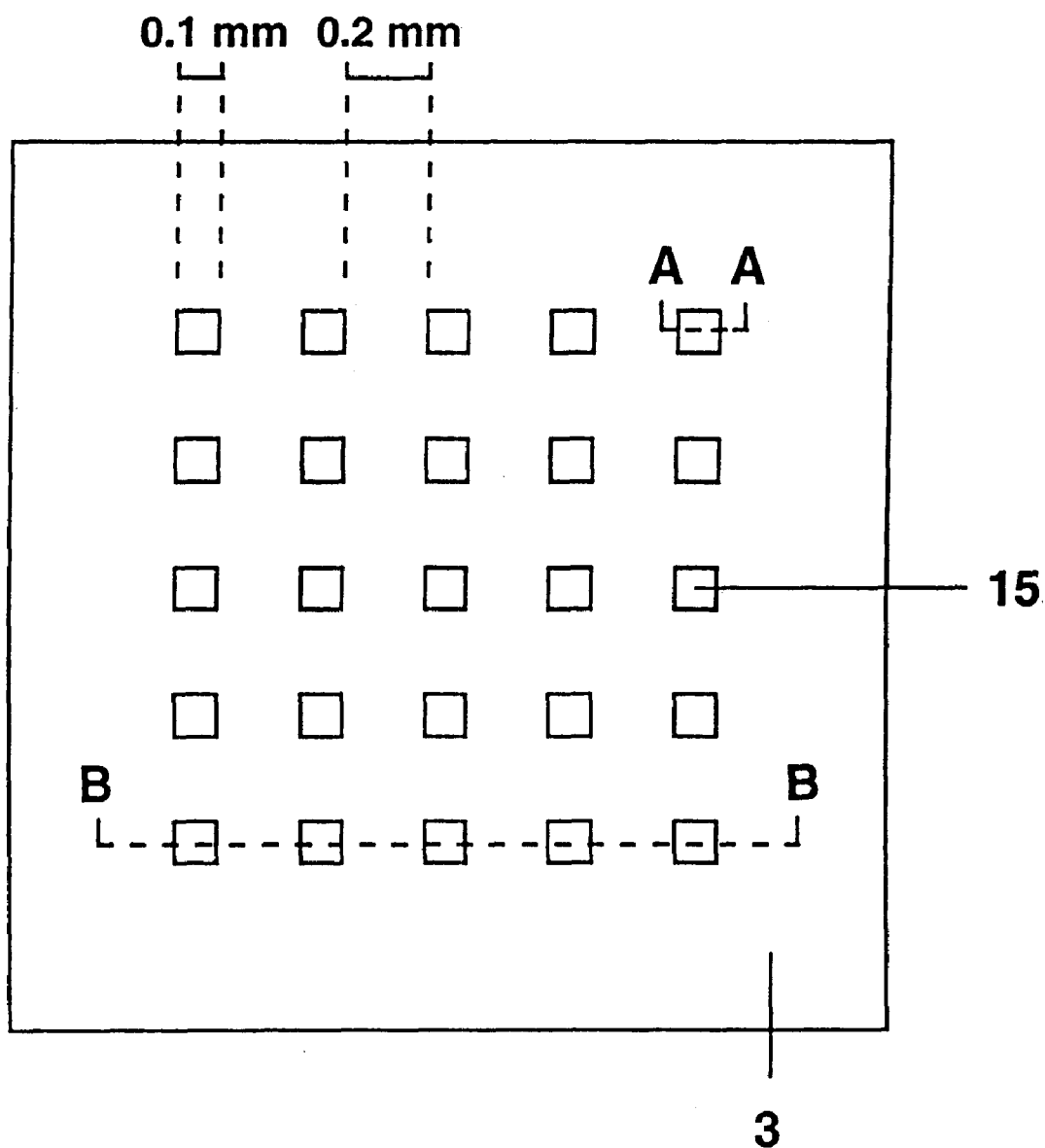
FIG. 1 shows the top view of an array of monolayer-covered patches.

A variety of protein arrays, methods, and protein-coated substrates useful for high-throughput drug screening, clinical diagnostics, and related processes are provided by the present invention.

(a) Definitions

The term "substrate" as used herein refers to the bulk, underlying, and core material of the devices or arrays or other embodiments of the invention.

The terms "micromachining" and "microfabricating" are both used herein to refer to any number of techniques which are useful in the generation of microstructures (structures of sub-millimeter scale). Such technologies include, but are not limited to, laser ablation, sputtering, electrodeposition, low-pressure vapor deposition, photolithography, and etching. Related technologies such as LIGA are also included. Most of these techniques were originally developed for use in semiconductors, microelectronics, and microelectromechanical systems but are applicable to the present invention as well.

The term "coating" is used herein to refer to a layer that is either formed on or applied to the surface of the substrate. For instance, exposure of a substrate, such as silicon, to air can result in oxidation of the exposed surface. In the case of a substrate made of silicon, a silicon oxide coating is formed on the surface upon exposure to air. In other instances, the coating is in no way derived from the substrate and may be placed upon the surface via mechanical, electrical, or chemical means. An example of this type of coating would be a metal coating that is applied to a polymer substrate. Although a coating may be of any thickness, typically the coating has a thickness smaller than that of the substrate.

An "interlayer" is a second coating or layer that is positioned between the first coating and the substrate. The primary purpose of a typical interlayer is to aid adhesion between the first coating and the substrate. One such example is the use of a titanium interlayer to help attach a gold coating to a silicon chip. However, other possible functions of an interlayer are also anticipated. For instance, some interlayers may perform a role in the detection system of the device.

The term "affinity tag" is used herein to refer to a functional moiety capable of immobilizing a protein onto the exposed functionality of a monolayer. In some cases, the affinity tag may be a simple chemical functional group. Other possibilities include amino acids, polypeptides, proteins, lipid bilayers, or a hydrogel. The affinity tag may be either covalently or noncovalently attached to the protein (via chemical conjugation or as a fusion protein, for instance). Likewise, the affinity tag may bind to the monolayer either covalently or noncovalently.

An "adaptor molecule", for purposes of this invention, is any entity that links an affinity tag to a protein. The adaptor molecule need not necessarily be a discrete molecule that is noncovalently attached to both the affinity tag and the protein. The adaptor molecule can be covalently attached to the affinity tag or the protein or both (via chemical conjugation or as a fusion protein, for instance). In some cases, an affinity tag may also be an internal part of the protein, such as an amino acid. Examples of adaptor molecules include polypeptides, proteins, membrane anchors, and biotin.

A "monolayer" is a single-molecule thick layer of organic molecules on a surface. A monolayer may be disordered or ordered. One face of the monolayer is composed of chemical functionalities on the termini of the organic molecules that are chemisorbed or physisorbed onto the surface material (headgroups). The other face of the monolayer is exposed and may bear any number of chemical functionalities (end groups). Preferably, the molecules of the monolayer are highly ordered and tightly packed, largely due to hydrophobic and van der Waals interactions between the molecules.

An "array", as used herein, refers to a two-dimensional pattern.

The terms "polypeptide" and "protein" are used interchangeably herein to refer to a polymer of amino acid residues. These terms also apply to amino acid polymers in which one or more amino acid residues is an artificial chemical analogue of a corresponding naturally occurring amino acid, as well as to naturally occurring amino acid polymers. An amino acid polymer in which one or more amino acid residues is an "unnatural" amino acid, not corresponding to any naturally occurring amino acid, is also encompassed by the use of the terms "protein" and "polypeptide" herein.

Proteins are considered herein to be members of the same "protein family" or to be "related" if they show significant similarities in structure and/or function, as would be recognized by one of ordinary skill in the art. Related proteins can be identified by sequence homology searches of DNA and protein databases using standard bioinformatics resources and software packages (examples of public databases: NCBI, NIH, EMBL, SwissProt, Brookhaven database, Washington University—Merck; private databases: Incyte, Hyseq, Human Genome Science; examples of software packages include EMOTIF, Blast, Fasta, Multalign, GCG Wisconsin University). Enzymatically related proteins of non-homologous sequence can be identified by one of ordinary skill in the art by screening the scientific literature (example: Medline database).

The term "fusion protein" refers to a protein composed of two or more polypeptides that, although typically unjoined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological condition" is used herein to refer to conditions that are typical inside a living organism or a cell. While it is recognized that some organs or organisms provide extreme conditions, the intra-organismal and intra-cellular environment normally varies around pH 7 (i.e. from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

(b) Protein-coated Substrates and Arrays.

In another embodiment, the present invention also provides a protein-coated substrate comprising a plurality of patches arranged in discrete, known regions on a substrate, where each of the patches comprises an immobilized protein with a different, known sequence and where each of the patches is separated from neighboring patches by from about 50 nm to about 500 $\mu$m. In a preferred embodiment, the protein-coated substrate comprises 9 or more patches.

Biosensors, micromachined devices, and medical devices that contain the protein-coated substrate comprising a plurality of patches arranged in discrete, known regions on substrate, where each of the patches comprises an immobilized protein with a different, known sequence and where each of the patches is separated from neighboring patches by from about 50 nm to about 500 $\mu$m are also contemplated.

Arrays of proteins are also provided by the present invention. In one embodiment, the protein arrays comprise micrometer-scale, two-dimensional patterns of proteins immobilized on arrays of functionalized surface patches.

In one embodiment, the array of proteins comprises a plurality of patches, preferably 9 or more, arranged in discrete known regions on a substrate, wherein each of the patches comprises an immobilized protein with a different, known sequence and wherein each of the patches is separated from neighboring patches by from about 50 nm to about 500 µm. In a preferred embodiment, the patches are separated from neighboring patches from about 200 nm to about 500 µm.

In some versions of the array, the diameter of each of the patches is proportional to the distance separating the patches. Therefore, the area of each patch may be from about 100 $nm^2$ to about 40,000 $µm^2$. Each patch preferably has an area from about 1 $µm^2$ to about 10,000 $µm^2$.

In one embodiment of the array, the array comprises 9 or more patches within a total area of 1 $cm^2$. In preferred embodiments of the array, the array comprises 100 or more patches within a total area of 1 $cm^2$. In another embodiment, the array comprises $10^3$ or more patches within a total area of 1 $cm^2$.

In one embodiment of the array, the protein immobilized on one patch differs from the protein immobilized on a second patch of the same array.

In another embodiment of the present invention, although the biological moiety of one reactive site is different from that of another, the two biological moieties are related. In a preferred embodiment, the two different proteins are members of the same protein family. The different proteins on the invention array may be either functionally related or just suspected of being functionally related. In another embodiment of the invention array, however, the function of the immobilized proteins may be unknown. In this case, the different proteins on the different patches of the array share a similarity in structure or sequence or are simply suspected of sharing a similarity in structure or sequence. Alternatively, the immobilized proteins may be just fragments of different members of a protein family.

The proteins immobilized on the array of the invention may be members of a protein family such as a receptor family (examples: growth factor receptors, catecholamine receptors, amino acid derivative receptors, cytokine receptors, lectins), ligand family (examples: cytokines, serpins), enzyme family (examples: proteases, kinases, phosphatases, ras-like GTPases, hydrolases), and transcription factors (examples: steroid hormone receptors, heat-shock transcription factors, zinc-finger, leucine-zipper, homeodomain). In one embodiment, the different immobilized proteins are all HIV proteases or hepatitis C virus (HCV) proteases. In an alternative embodiment, the protein immobilized on each patch is a different antibody or antibody fragment (Fab, for example).

In an alternative embodiment of the invention array, the proteins on different patches are identical.

The substrate of the array may be either organic or inorganic, biological or non-biological, or any combination of these materials. In one embodiment, the substrate is transparent or translucent. The portion of the surface of the substrate on which the patches reside is preferably flat and firm or semi-firm. Numerous materials are suitable for use as a substrate in the array embodiment of the invention. For instance, the substrate of the invention array can comprise a material selected from a group consisting of silicon, silica, quartz, glass, controlled pore glass, carbon, alumina, titanium dioxide, germanium, silicon nitride, zeolites, and gallium arsenide. Many metals such as gold, platinum, aluminum copper, titanium, and their alloys are also options for substrates of the array. In addition, many ceramics and polymers may also be used as substrates. Polymers which may be used as substrates include, but are not limited to, the following: polystyrene; poly(tetra)fluorethylene; (poly) vinylidenedifluoride; polycarbonate; polymethylmethacrylate; polyvinylethylene; polyethyleneimine; poly(etherether) ketone; polyoxymethylene (POM); polyvinylphenol; polylactides; polymethacrylimide (PMI); polyalkenesulfone (PAS); polyhydroxyethylmethacrylate; polydimethylsiloxane; polyacrylamide; polyimide; co-block-polymers; and Eupergit®. Photoresists, polymerized Langmuir-Blodgett films, and LIGA structures may also serve as substrates in the present invention. The preferred substrates for the array comprise silicon, silica, glass, or a polymer.

In a preferred embodiment of the invention array, the patches further, comprise a monolayer on the surface of the substrate and the proteins of the patches are immobilized on the monolayer. The monolayer is preferably a self-assembling monolayer. This monolayer may optionally comprise molecules of the formula X-R-Y, wherein R is a spacer, X is a functional group that binds R to the surface, and Y is a functional group for binding proteins onto the monolayer.

A variety of chemical moieties may function as monolayers in the array of the present invention. However, three major classes of monolayer formation are preferably used to expose high densities of bioreactive omega-functionalities on the patches of the array: (i) alkylsiloxane monolayers ("silanes") on hydroxylated surfaces (as taught in, for example, U.S. Pat. No. 5,405,766, PCT Publication WO 96/38726, U.S. Pat. No. 5,412,087, and 5,688,642); (ii) alkyl-thiol/dialkyldisulfide monolayers on noble metals (preferably Au(111)) (as, for example, described in Allara et al., U.S. Pat. No. 4,690,715; Bamdad et al., U.S. Pat. No. 5,620,850; Wagner et al., *Biophysical Journal*, 1996, 70:2052–2066); and (iii) alkyl monolayer formation on oxide-free passivated silicon (as taught in, for example, Linford et al., *J. Am. Chem. Soc.*, 1995, 117:3145–3155, Wagner et al., *Journal of Structural Biology*, 1997, 119:189–201, U.S. Pat. No. 5,429,708). One of ordinary skill in the art, however, will recognize that many possible moieties may be substituted for X R, and/or Y, dependent primarily upon the choice of substrate, coating, and affinity tag. Many examples of monolayers are described in Ulman, *An Introduction to Ultrathin Organic Films: From Langmuir-Blodgett to Self Assembly*, Academic press (1991).

An array of the present invention may optionally further comprise a coating between the substrate and the monolayer of its patches. This coating may either be formed on the substrate or applied to the substrate. The substrate can be modified with a coating by using thin-film technology based on either physical vapor deposition (PVD) or plasma-enhanced chemical vapor deposition (PECVD). Alternatively, plasma exposure can be used to directly activate the substrate. For instance, plasma etch procedures can be used to oxidize a polymeric surface (i.e. polystyrene or polyethylene to expose polar functionalities such as hydroxyls, carboxylic acids, aldehydes and the like).

The coating may comprise a metal film. Possible metal films include aluminum, chromium, titanium, nickel, stainless steel, zinc, lead, iron, magnesium, manganese, cadmium, tungsten, cobalt, and alloys or oxides thereof. In a preferred embodiment, the metal film is a noble metal film. Noble metals that may be used for a coating include, but are not limited to, gold, platinum, silver, copper, and palladium. In an especially preferred embodiment, the coating comprises gold or a gold alloy. Electron-beam evaporation may be used to provide a thin coating of gold on the surface. In a preferred embodiment, the metal film is from about 50 nm to about 500 nm in thickness.

In alternative embodiments, the coating comprises a composition selected from the group consisting of silicon, silicon oxide, silicon nitride, silicon hydride, indium tin oxide, magnesium oxide, alumina, glass, hydroxylated surfaces, and a polymer.

If the patches comprise a coating between the substrate and the monolayer, then it is understood that the coating must be composed of a material for which a suitable functional group X is available (see below). If no such coating is present, then it is understood that the substrate must be composed of a material for which a suitable functional group X is available.

In one embodiment of the invention array, the surface of the coating is ultraflat. In this embodiment, the mean roughness of the surface of the coating is less than about 5 angstroms for areas of at least 25 $\mu m^2$. In a preferred embodiment, the mean roughness of the surface of the coating is less than about 3 angstroms for areas of at least 25 $\mu m^2$. The ultraflat coating can optionally be a template-stripped surface as described in Hegner et al., *Surface Science*, 1993, 291:39–46 and Wagner et al., Langmuir, 1995, 11:3867–3875, both of which are incorporated herein by reference.

It is contemplated that the coatings of many arrays will require the addition of at least one adhesion layer between said coating and said substrate. Typically, the adhesion layer will be at least 10 angstroms thick and may be much thicker. For instance, a layer of titanium may be desirable between a silicon wafer and a gold coating. In an alternative embodiment, an epoxy glue such as Epo-tek 377®, Epo-tek 301-2®, (Epoxy Technology Inc., Billerica, Mass.) may be preferred to aid adherence of the coating to the substrate. Determinations as to what material should be used for the adhesion layer would be obvious to one skilled in the art once materials are chosen for both the substrate and coating. In other embodiments, additional adhesion mediators or interlayers may be necessary to improve the optical properties of the array, for instance, in waveguides for detection purposes.

Deposition or formation of the coating (if present) on the substrate is done prior to the formation of patches of bioreactive monolayers thereon. Monolayer-compatible surface patches may optionally be fabricated by photolithography, micromolding (PCT Publication WO 96/29629), wet chemical etching, or any combination of these. Bio-reactive monolayers are then formed on the patches. Alternatively, arrays of bioreactive-monolayer functionalized surface patches can be created by microstamping (U.S. Pat. Nos. 5,512,131 and 5,731,152) or microcontact printing ($\mu$CP) (PCT Publication WO 96/29629). Subsequent immobilization of biomolecules results in two-dimensional protein arrays. Inkjet chemical dispensers provide another option for patterning monolayer X-R-Y molecule or components thereof to nanometer or micrometer scale sites on the surface of the substrate or coating (Lemmo et al., *Anal Chem.*, 1997, 69:543–551).

Diffusion boundaries between the patches may be integrated as topographic patterns or surface functionalities with orthogonal wetting behavior. For instance, walls of substrate material or photoresist may be used to separate some of the patches from some of the others or all of the patches from each other. In a preferred embodiment, the patches are separated from each other by surfaces free of monolayers of the form X-R-Y. Alternatively, non-bioreactive monolayers with different wettability may be used to separate patches from one another.

FIG. 1 shows the top view of one example of a monolayer-covered array. On the array, a number of patches 15 cover the surface of the substrate 3.

Figure 2:
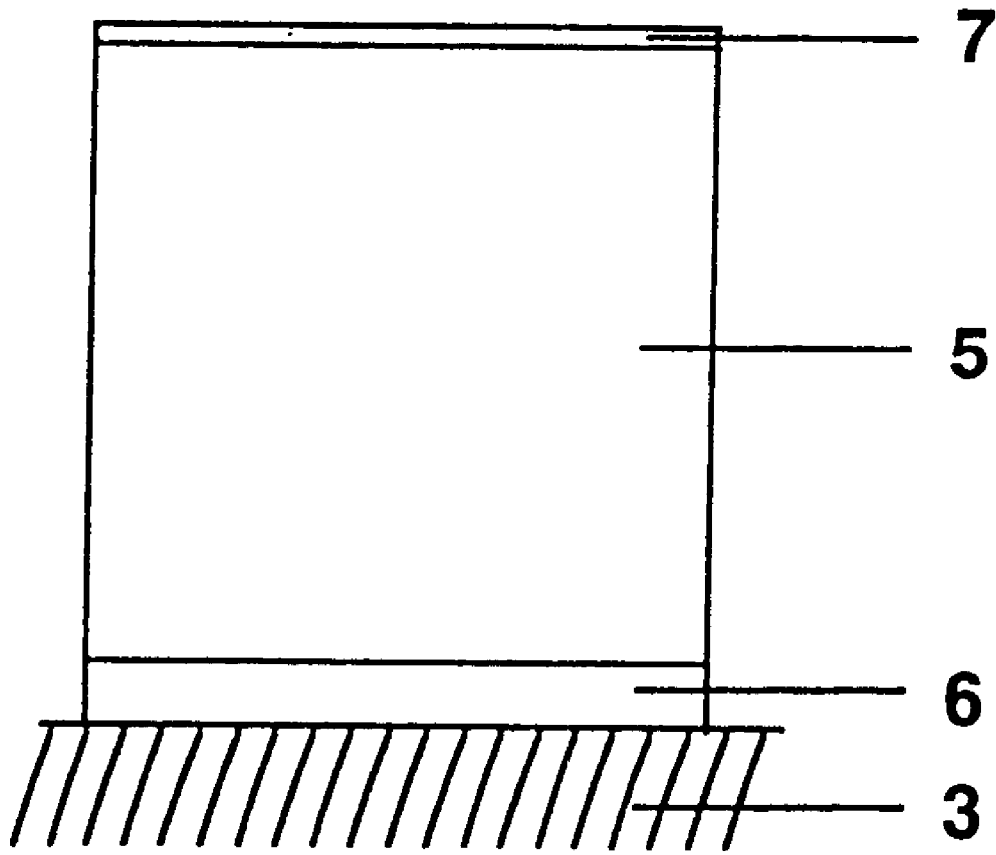
FIG. 2 shows the cross section of an individual patch of the array of FIG. 1.

FIG. 2 shows a detailed cross section of a patch of the array of FIG. 1. This view illustrates the use of a coating 5 on the substrate 3. An adhesion interlayer 6 is also included in the patch. On top of the patch resides a monolayer 7.

Figure 3:
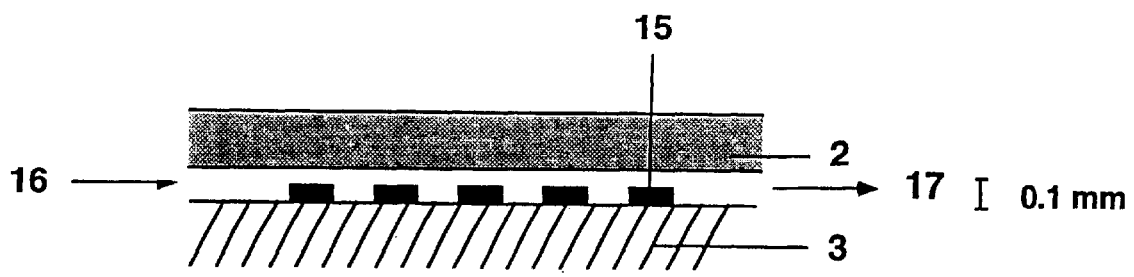
FIG. 3 shows the cross section of a row of monolayer-covered patches of the array of FIG. 1.

FIG. 3 shows a cross section of one row of the monolayer-covered patches 15 of the array of FIG. 1. This figure also shows the use of a cover 2 over the array. Use of the cover 2 creates an inlet port 16 and an outlet port 17 for solutions to be passed over the array.

If the patches of the invention array comprise a monolayer of molecules of the formula X-R-Y, then R may comprise a hydrocarbon chain from about 1 to about 200 carbons long. The hydrocarbon chain may comprise an alkyl, aryl, alkenyl, alkynyl, cycloalkyl, alkaryl, aralkyl group, or any combination thereof. In a preferred embodiment, R is an alkyl chain from about 8 to about 22 carbons long and is optionally a straight alkane. However, it is also contemplated that in an alternative embodiment, R may readily comprise a hydrocarbon chain from about 2 to about 200 carbons long and be interrupted by at least one hetero atom. The interrupting hetero groups can include —O—, —CONH—, —CONHCO—, —NH—, —CSNH—, —CO—, —CS—, —S—, —SO—, —(OCH$_2$CH$_2$)$_n$— (where n=1–20), —(CF$_2$)$_n$— (where n=1–22), and the like. Alternatively, one or more of the hydrogen moieties of R can be substituted with deuterium.

X may be chosen as any group which affords chemisorption or physisorption of the monolayer onto the surface of the substrate (or the coating, if present). When the substrate or coating is a metal or metal alloy, X, at least prior to incorporation into the monolayer, can in one embodiment be chosen to be an asymmetrical or symmetrical disulfide, sulfide, diselenide, selenide, thiol, isonitrile, selenol, a trivalent phosphorus compound, isothiocyanate, isocyanate, xanthanate, thiocarbamate, a phosphine, an amine, thio acid or a dithio acid. This embodiment is especially preferred when a coating or substrate is used that is a noble metal such as gold, silver, or platinum.

If the substrate of the array is a material such as silicon, silicon oxide, indium tin oxide, magnesium oxide, alumina, quartz, glass, or silica, then a preferred embodiment of the invention array comprises an X that, prior to incorporation into said monolayer, is a monohalosilane, dihalosilane, trihalosilane, trialkoxysilane, dialkoxysilane, or a monoalkoxysilane. In preferred embodiments, X is a trichlorosilane or trialkoxysilane.

In other embodiments, the surface of the substrate (or coating thereon) is composed of a metal oxide such as titanium oxide, tantalum oxide, indium tin oxide, magnesium oxide, or alumina and X is a carboxylic acid. Alternatively, if the surface of the substrate (or coating thereon) of the device is copper, then X may optionally be a hydroxamic acid.

If the substrate used in the invention is a polymer, then in many cases a coating on the substrate such as a copper coating will be included in the device. An appropriate functional group X for the coating would then be chosen for use in the device. In an alternative embodiment comprising a polymer substrate, the surface of the polymer may be plasma-modified to expose desirable surface functionalities for monolayer formation. For instance, EP 780423 describes the use of a monolayer molecule that has an alkene X functionality on a plasma exposed surface. Still another possibility for the invention device comprised of a polymer is that the surface of the polymer on which the monolayer is formed is functionalized due to copolymerization of appropriately functionalized precursor molecules.

Another possibility is that prior to incorporation into the monolayer, X can be a free-radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyano compounds and isonitrile compounds can be used for X, if the reaction with X is accompanied by ultraviolet, infrared, visible, or microwave radiation.

In alternative embodiments, X, prior to incorporation into the monolayer, may be a hydroxyl, carboxyl, vinyl, sulfonyl, phosphoryl, silicon hydride, or an amino group.

The component, Y, of the monolayer is a functional group responsible for binding a protein onto the monolayer. In a preferred embodiment of the invention, the Y group is either highly reactive (activated) towards the protein or is easily converted into such an activated form. In a preferred embodiment, the coupling of Y with the protein occurs readily under normal physiological conditions not detrimental to the biological activity of the protein. The functional group Y may either form a covalent linkage or a noncovalent linkage with the protein (or its affinity tag, if present). In a preferred embodiment, the functional group Y forms a covalent linkage with the protein or its affinity tag. It is understood that following the attachment of the protein to Y, the chemical nature of Y may have changed.

In one embodiment of the array of the present invention, Y is a functional group that is activated in situ. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Appropriate modes of activation would be obvious to one skilled in the art. Alternatively, Y can comprise a functional group that requires photoactivation prior to becoming activated enough to trap the biological moiety.

In an especially preferred embodiment of the array of the present invention, Y is a complex and highly reactive functional moiety that is compatible with monolayer formation and needs no in situ activation prior to reaction with the protein and/or affinity tag. Such possibilities for Y include, but are not limited to, maleimide, N-hydroxysuccinimide (Wagner et al., *Biophysical Journal*, 1996, 70:2052–2066), nitrilotriacetic acid (U.S. Pat. No. 5,620,850), activated hydroxyl, haloacetyl, bromoacetyl, iodoacetyl, activated carboxyl, hydrazide, epoxy, aziridine, trifluoromethyldiaziridine, pyridyldisulfide, N-acyl-imidazole, imidazolecarbamate, succinimidylcarbonate, arylazide, anhydride, diazoacetate, benzophenone, isothiocyanate, isocyanate, imidoester, fluorobenzene, and biotin.

Figure 4:
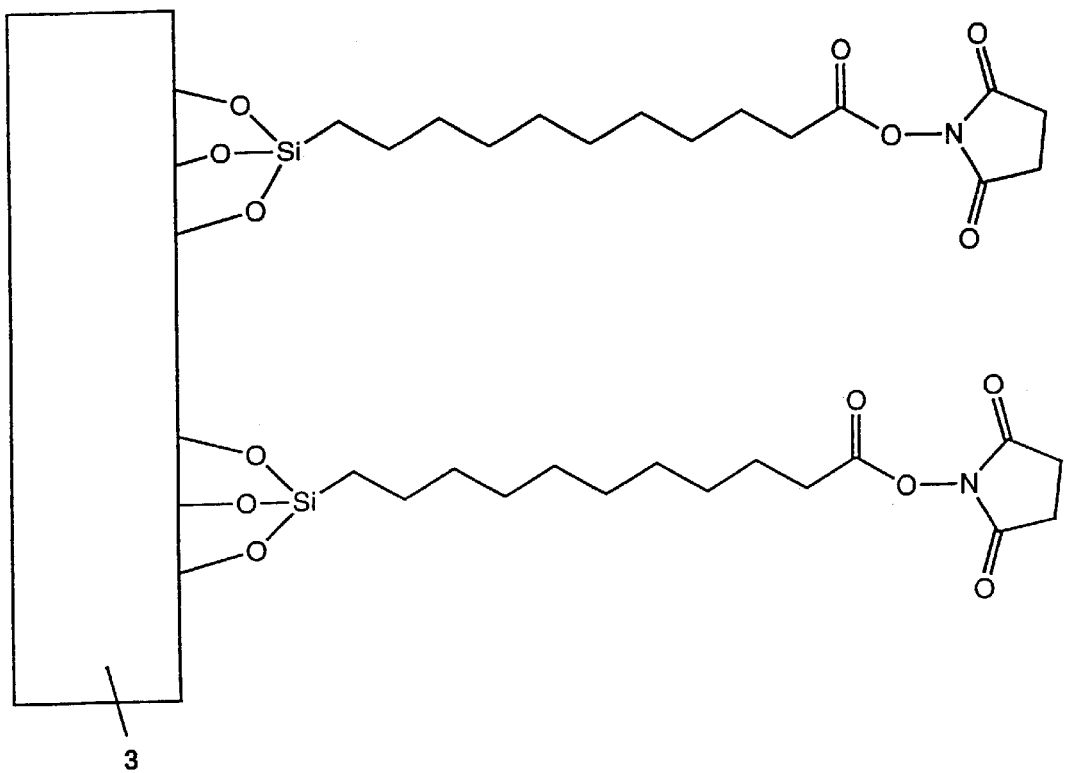
FIG. 4 shows aminoreactive monolayer molecules on a substrate.

FIG. 4 shows one example of a monolayer on a substrate 3. In this example, substrate 3 comprises silicon (having a silicon oxide surface). The monolayer is aminoreactive because it bears a functional group Y that is N-hydroxysuccinimide.

Figure 5:
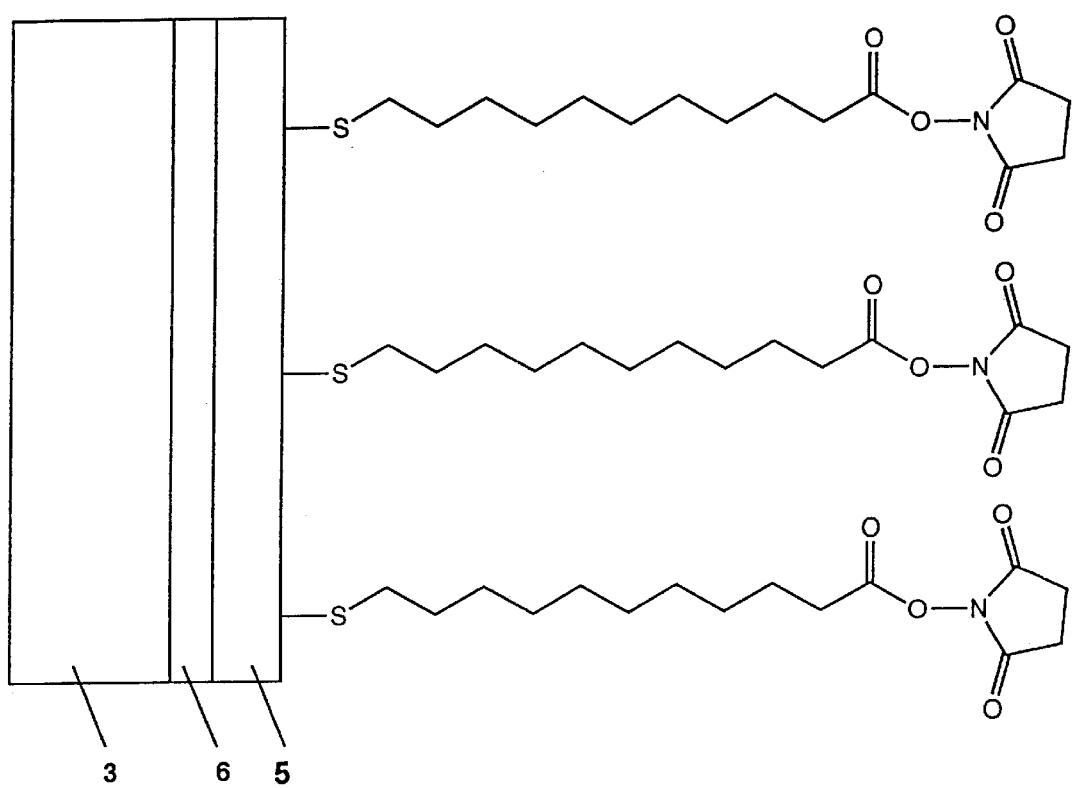
FIG. 5 shows aminoreactive monolayer molecules on a coated substrate.

FIG. 5 shows another example of a monolayer on a substrate 3. In this case, however, a thin film coating 5 comprised of gold covers the surface of the substrate 3. Also, in this embodiment, an adhesion interlayer 6 is used to adhere the coating 5 to the substrate 3 and is comprised of titanium. This monolayer is also aminoreactive because it bears a functional group Y that is N-hydroxysuccinimide.

In an alternative embodiment, the functional group Y of the array is selected from the group of simple functional moieties. Possible Y functional groups include, but are not limited to, —OH, —NH$_2$, —COOH, —COOR, —RSR, —PO$_4^{-3}$, OSO$_3^{-2}$, —SO$_3^-$, —COO$^-$, —SOO$^-$, —CONR$_2$, —CN, —NR$_2$, and the like. Simple groups such as these are only preferred for Y when the affinity tag of the invention composes a layer of affinity tag molecules (such as polylysine) that coats the exposed portion of the monolayer prior to immobilization of the biological moiety (see below).

The monolayer molecules of the present invention can optionally be assembled on the surface in parts. In other words, the monolayer need not necessarily be constructed by chemisorption or physisorption of molecules of the formula X-R-Y to the surface of the substrate (or coating). Instead, in one embodiment, X may be chemisorbed or physisorbed to the surface of the substrate (or coating) alone first. Then, R or even just individual components of R can be attached to X through a suitable chemical reaction. Upon completion of addition of the spacer R to the X moiety already immobilized on the surface, Y can be attached to the ends of the monolayer molecule through a suitable covalent linkage.

Not all monolayer molecules on a given patch need be identical to one another. Some may consist of mixed monolayers. For instance, the monolayer of an individual patch may optionally comprise at least two different X-R-Y molecules. This second X-R-Y molecule may immobilize the same or a different protein from the first. In addition, some of the monolayer molecules X-R-Y of a patch may have failed to attach any protein.

As another alternative of the invention, the monolayer of an individual patch on the array may comprise a second molecule that is of the formula, X-R-V where R is a spacer, X is a functional group that binds R to the surface, and V is a moiety resistant to the non-specific binding of proteins. V must also be biocompatible with proteins. Typically, V will consist of a hydroxyl, saccharide, or polyethylene glycol moiety (EP Publication 780423).

As a still further alternative of the invention array, the array may further comprise at least one unreactive patch devoid of protein, wherein said patch comprises a monolayer of molecules of the formula X-R-V, where R is a spacer, X is a functional group that binds R to the surface, and V is a moiety resistant to the non-specific binding of proteins.

Regardless of the nature of the monolayer molecules, in some arrays it may be desirable to provide crosslinking between molecules of an individual patch's monolayer. In general, crosslinking confers additional stability to the monolayer. Such methods are familiar to those skilled in the art (for instance, see Ulman, *An Introduction to Ultrathin Organic Films: From Langmuir-Blodgett to Self-Assembly*, Academic Press (1991)).

After completion of the monolayer, the protein may be attached to the monolayer via interaction with the Y-functional group. Y-functional groups which fail to react with any protein molecules are preferably quenched prior to use of the array.

In a preferred embodiment, the array further comprises an affinity tag that enhances site-specific immobilization of the biological moiety onto the monolayer. The use of an affinity tag on the proteins of the array allows for at least one of two advantages. An affinity tag can confer enhanced binding or reaction of the protein with Y. This enhancement effect may be either kinetic or thermodynamic. The affinity tag/Y-functional group pair used in the patches of the array preferably allows for immobilization of the biological molecules in a manner which does not require harsh reaction conditions that are adverse to protein stability or function. In most embodiments, immobilization in aqueous, biological buffers are ideal. An affinity tag also preferably offers immobilization that is specific to a designated site or location on the biological moiety. For this to occur, attachment of the affinity tag to the protein must be site-specific. This site specific immobilization helps ensure that the reactive site of the protein remains accessible to ligands in solution. Another advantage of immobilization through affinity tags is that it allows for a common immobilization strategy to be used with multiple, different proteins.

In a preferred embodiment, the affinity tag comprises at least one amino acid. The affinity tag may be a polypeptide comprising at least one monolayer-reactive amino acid. Alternatively, the affinity tag may be a lone, monolayer-reactive amino acid. Examples of possible monolayer-reactive amino acids include cysteine, lysine, histidine, arginine, tyrosine, and glutamine. A polypeptide or amino acid affinity tag is preferably expressed as a fusion protein with the biological moiety. Amino acid tags provide either a single amino acid or a series of amino acids that can interact with the Y-functional group of the monolayer molecules. Amino acid affinity tags can be readily introduced into recombinant proteins to facilitate oriented immobilization by covalent binding to the bioreactive Y-functional group of the monolayer.

The affinity tag may comprise a poly(amino acid) tag. A poly(amino acid) tag is a polypeptide that comprises from about 2 to about 100 residues of a single amino acid, optionally interrupted by residues of other amino acids. For instance, the affinity tag may comprise a poly-cysteine, polylysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given Y-functionality.

The position of the amino acid tag can be at the amino-, or carboxy-terminus of the protein or anywhere in-between. Where compatible with protein function, affinity tags introduced for protein purification are preferentially located at the C-terminus of the recombinant protein to ensure that only full-length proteins are isolated during protein purification.

Affinity tags may also contain one or more unnatural amino acids. Unnatural amino acids can be introduced using suppressor tRNAs that recognize stop codons (i.e. amber) (Noren et al., *Science*, 1989, 244:182–188; Ellman et al., *Methods Enzym.*, 1991, 202:301–336; Cload et al., *Chem. Biol.*, 1996, 3:1033–1038). The tRNAs are chemically amino-acylated to contain chemically altered ("unnatural") amino acids for use with specific coupling chemistries (i.e. ketone modifications, photoreactive groups).

In an alternative embodiment the affinity tag can comprise a whole protein, such as, but not limited to, glutathione S-transferase, an antibody, avidin, or streptavidin.

Other protein conjugation and immobilization techniques known in the art may be adapted for the purpose of immobilizing proteins on activated monolayers. For instance, in an alternative embodiment of the array, the affinity tag may be an organic bioconjugate which is chemically coupled to the protein of interest. Biotin or antigens may be chemically cross linked to the protein. Alternatively, a chemical cross linker may be used that attaches a simple functional moiety such as a thiol or an amine to the surface of a protein.

Figure 6:
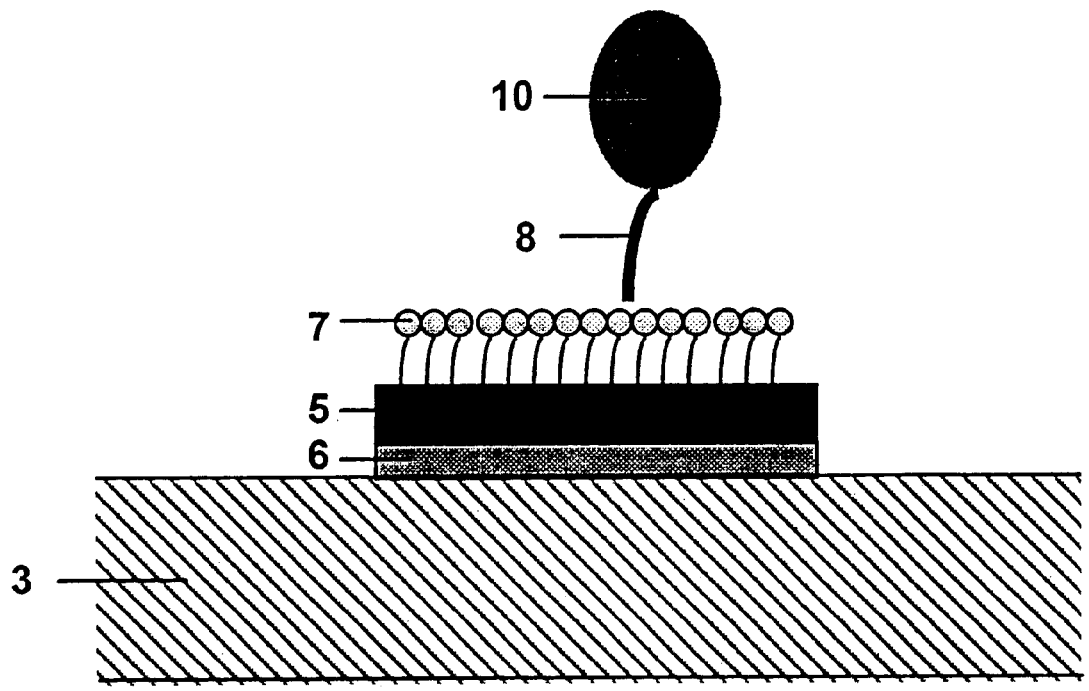
FIG. 6 shows the immobilization of a protein on a monolayer-coated substrate via an affinity tag.

FIG. 6 shows a detailed cross section of a patch on one embodiment of the invention array. In this embodiment, a protein 10 is immobilized on a monolayer 7 on a substrate 3. An affinity tag 8 connects the biological moiety 10 to the monolayer 7. The monolayer 7 is formed on a coating 5 which is separated from the substrate 3 by an interlayer 6.

In an alternative embodiment of the array invention, the affinity tag is a component of a layer of affinity tag molecules immobilized on the monolayer of an individual patch. For instance, a hydrogel composed of a material such as dextran can serve as a suitable layer of affinity tag molecules in the array. Use of such hydrogels to immobilize biological moieties is described in U.S. Pat. No. 5,242,828. Poly-lysine is another option for a material useful in forming an affinity-tag layer (for an example see U.S. Pat. No. 5,629,213). The layer of affinity tag molecules could also constitute a phospholipid bilayer or a phospholipid monolayer as described in PCT Publication WO 96/38726. Use of a phospholipid monolayer or bilayer as an affinity tag would be suitable if the biological moiety to be immobilized is a membrane protein, such as an ion channel protein.

If the proteins of different patches on the array are different, then different solutions, each containing an affinity-tagged protein, must be delivered to their individual patches. Protein solutions may be transferred to the appropriate patches via noncontact printing using a microdelivery device employing a ball-point pen type of mechanism. Alternatively, microcapillary-based dispensing systems may be used. These dispensing systems are preferably computer-aided. The use of other microprinting techniques for transferring protein solutions to the bioreactive patches is also possible.

Another major embodiment of the arrays of the present invention comprises an adaptor molecule that links the affinity tag to the immobilized biological moiety. The additional spacing of the protein from the surface of the substrate (or coating) that is afforded by the use of an adaptor molecule is particularly advantageous since proteins are known to be prone to surface inactivation. One of ordinary skill in the art will be able to choose an adaptor molecule which is appropriate for a given affinity tag. For instance, if the affinity tag is streptavidin, then the adaptor could be a biotin molecule that is chemically conjugated to the protein which is to be immobilized. Alternatively, if the affinity tag is a phospholipid biolayer or monolayer then a membrane anchor could be chosen as a suitable adaptor molecule.

In a preferred embodiment, the adaptor molecule is a polypeptide, such as protein G or protein A. In a preferred embodiment, the affinity tag, adaptor molecule, and biological moiety together compose a fusion protein. Such a fusion protein may be readily expressed using standard recombinant DNA technology. Adaptor proteins are especially useful to increase the solubility of the protein of interest and to increase the distance between the surface of the substrate or coating and the protein of interest. Use of an adaptor protein or polypeptide can also be very useful in facilitating the preparative steps of protein purification by affinity binding prior to immobilization on the array. Examples of possible adaptor proteins include glutathione-S-transferase (GST), maltose-binding protein, chitin-binding protein, thioredoxin, green-fluorescent protein (GFP). GFP can also be used for quantification of surface binding.

Figure 7:
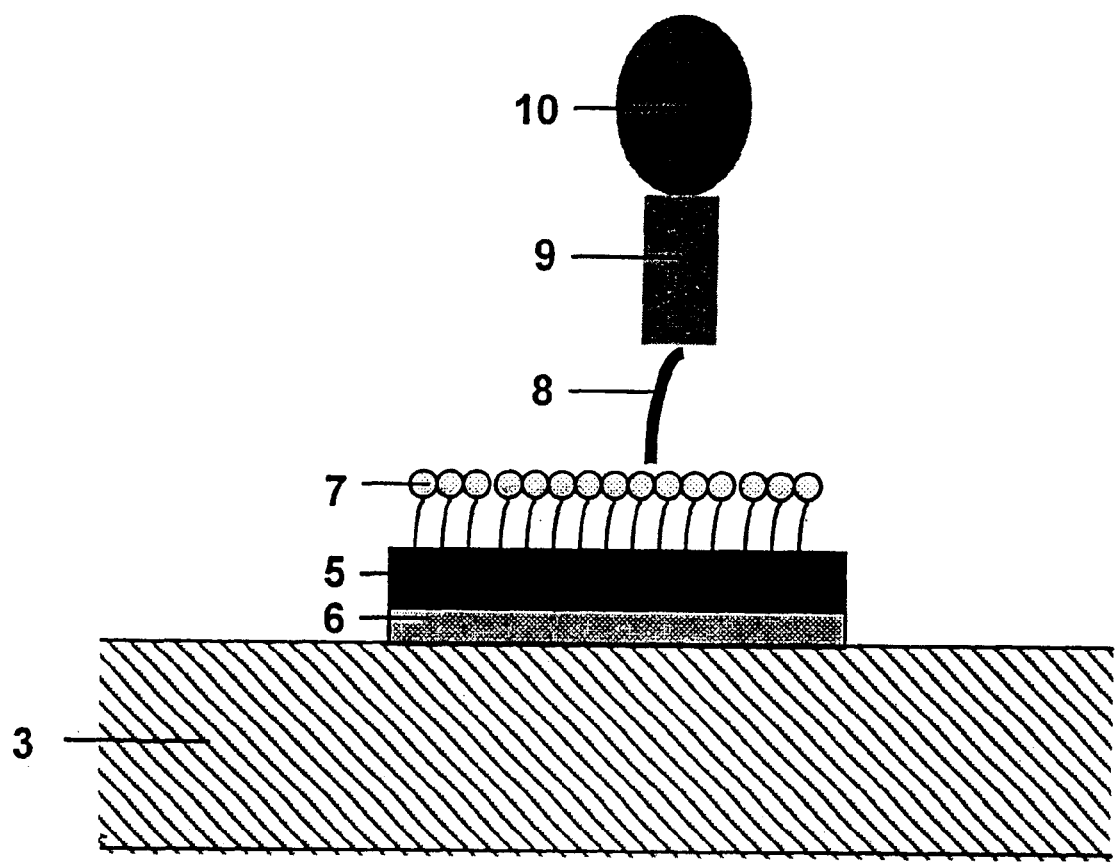
FIG. 7 shows the immobilization of a protein on a monolayer-coated substrate via an affinity tag and an adaptor.

FIG. 7 shows a cross section of a patch on one particular embodiment of the invention array. The patch comprises a protein 10 immobilized on a monolayer 7 via both an affinity tag 8 and an adaptor molecule 9. The monolayer 7 rests on a coating 5. An interlayer 6 is used between the coating 5 and the substrate 3.

In preparation for immobilization to the devices and arrays of the present invention, proteins can be expressed from recombinant DNA either in vivo or in vitro. Amino acid affinity tags are introduced by polymerase chain reaction. Expression in vivo is in either bacteria (*Escherichia coli*), lower eukaryotes (*Saccharomyces cerevisiae, Saccharomyces pombe, Pichia pastoris*) or higher eukaryotes (bacculo-infected insect cells, insect cells mammalian cells), or in vitro (*Escherichia coli* lysates, wheat germ extracts, reticulocyte lysates). Proteins are purified by affinity chromatography using commercially available resins.

DNA sequences encoding amino acid affinity tags and adaptor proteins are engineered into the expression vectors such that the genes of interest can be cloned in frame either 5' or 3' of the DNA sequence encoding the affinity tag and adaptor protein.

Figure 8:
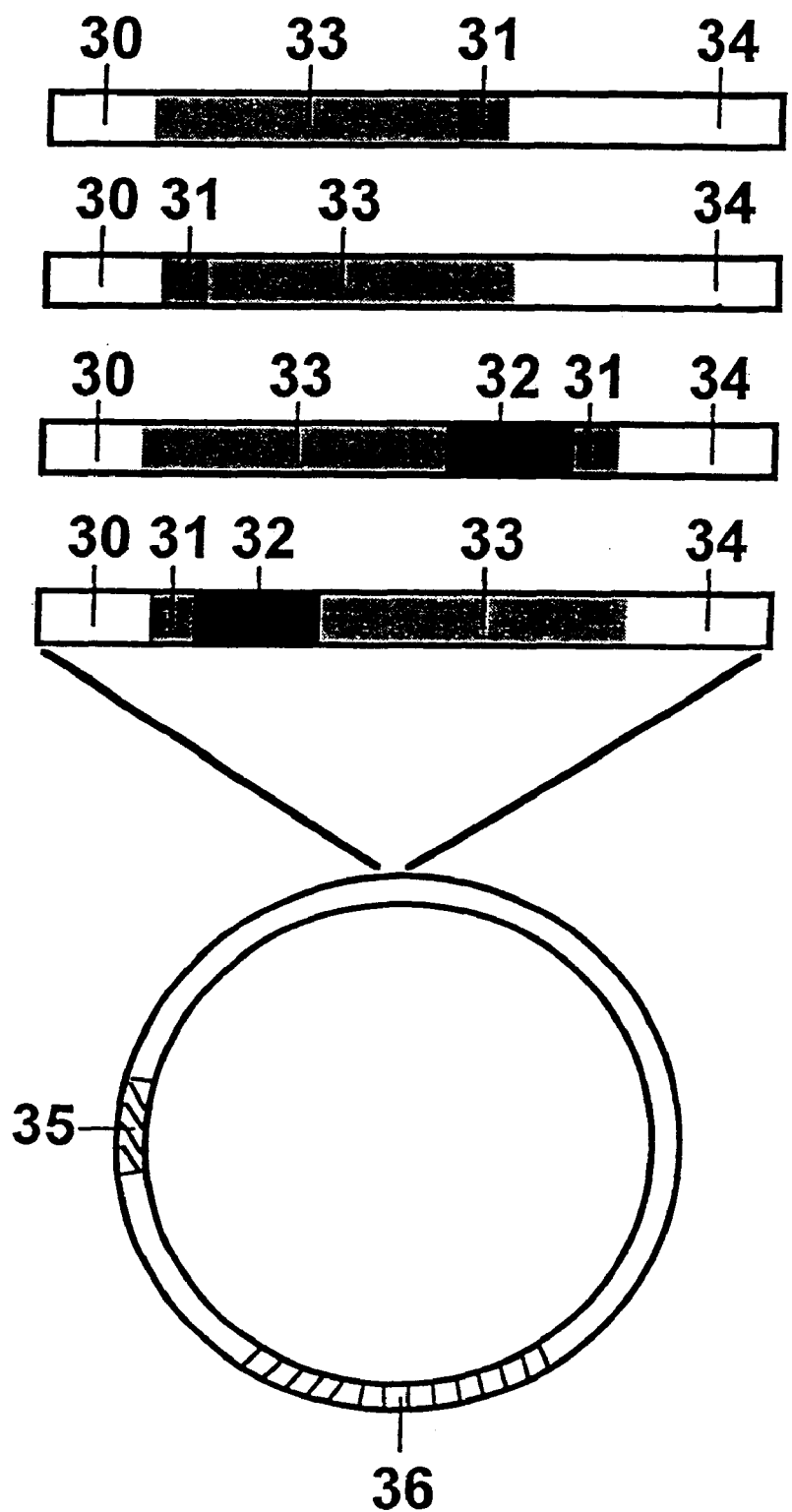
FIG. 8 shows four possible expression vectors useful for expressing fusion proteins of the desired protein, an affinity tag, and, optionally, an adaptor molecule.

FIG. 8 shows four possible expression vectors for expressing the protein of interest, a polypeptide affinity tag, and a polypeptide adaptor molecule as a fusion protein. The vector contains an origin of replication sequence 35 and a gene 36 capable of conferring antibiotic resistance to a host cell. The insert of the vector contains a promoter sequence 30 and a termination signal sequence 34. Between the sequences 30 and 34, the insert also contains a gene 33 encoding the protein of interest and sequence 31 encoding the polypeptide affinity tag. Sequence 32 which codes for a polypeptide adaptor molecule may also be included on the plasmid and is positioned between the protein and affinity-tag coding regions (33 and 31, respectively).

Preferably, production of families of related proteins involves parallel processing from cloning to protein expression and protein purification. cDNAs for the protein of interest will be amplified by PCR using cDNA libraries or EST (expressed sequence tag) clones as templates. For in vivo expression of the proteins, cDNAs can be cloned into commercial expression vectors (Qiagen, Novagen, Clontech) and introduced into the appropriate organism for expression (organisms include: *Escherichia coli, Saccharomyces cerevisiae, Saccharomyces pombe, Pichia pastoris*, bacculovirus/insect cells, insect cells, mammalian cells). For in vitro expression PCR-amplified DNA sequences are directly used in coupled in vitro transcription/translation systems (*Escherichia coli* S30 lysates from T7 RNA polymerase expressing, preferably protease-deficient strains, wheat germ lysates, reticulocyte lysates with and without microsomes (Promega, Pharmacia, Panvera)). The choice of organism for optimal expression depends on the extent of post-translational modifications (i.e. glycosylation, lipid-modifications).

*Escherichia coli* based protein expression will be the method of choice for soluble proteins that do not require extensive post-translational modifications for activity. Extracellular or intracellular domains of membrane proteins will be fused to protein adaptors for expression and purification.

The entire approach can be performed using 96-well assay plates. PCR reactions are carried out under standard conditions. Oligonucleotide primers contain unique restriction sites for facile cloning into the expression vectors. Alternatively, the TA cloning system (Clontech) can be used. Expression vectors contain the sequences for affinity tags and the protein adaptors. PCR products are ligated into the expression vectors (under inducible promoters) and introduced into the appropriate competent *Escherichia coli* strain by calcium-dependent transformation (strains include: XL-1 blue, BL21, SG13009(lon-)). Transformed *Escherichia coli* cells are plated and individual colonies transferred into 96-array blocks. Cultures are grown to mid-log phase, induced for expression, and cells collected by centrifugation. Cells are resuspended containing lysozyme and the membranes broken by rapid freeze/thaw cycles, or by sonication. Cell debris is removed by centrifugation and the supernatants transferred to 96-tube arrays. The appropriate affinity matrix is added, protein of interest bound and nonspecifically bound proteins removed by repeated washing steps using 12–96 pin suction devices and centrifugation. Alternatively, magnetic affinity beads and filtration devices can be used (Qiagen). The proteins are eluted and transferred to a new 96-well array. Protein concentrations are determined and an aliquot of each protein is spotted onto a nitrocellulose filter and verified by Western analysis using an antibody directed against the affinity tag. The purity of each sample is assessed by SDS-PAGE and Coomassie staining or mass spectroscopy. Proteins are snap-frozen and stored at −80° C.

*Saccharomyces cerevisiae* allows for core glycosylation and lipid modifications of proteins. The approach described above for *Escherichia coli* can be used with slight modifications for transformation and cell lysis. Transformation of *Saccharomyces cerevisiae* is by lithium-acetate and cell lysis is either by lyticase digestion of the cell walls followed by freeze-thaw, sonication or glass-bead extraction. Variations of post-translational modifications can be obtained by different yeast strains (i.e. *Saccharomyces pombe, Pichia pastoris*).

The advantage of the bacculovirus system or mammalian cells are the wealth of post-translational modifications that can be obtained. The bacculo-system requires cloning of viruses, obtaining high titer stocks and infection of liquid insect cell suspensions (cells are SF9, SF21). Mammalian cell-based expression requires transfection and cloning of cell lines. Soluble proteins are collected from the medium while intracellular or membrane bound proteins require cell lysis (either detergent solubilization, freeze-thaw). Proteins can then be purified analogous to the procedure described for *Escherichia coli*.

For in vitro translation the system of choice is *Escherichia coli* lysates obtained from protease-deficient and T7 RNA polymerase overexpressing strains. *Escherichia coli* lysates provide efficient protein expression (30–50 µg/ml lysate). The entire process is carried out in 96-well arrays. Genes of interest are amplified by PCR using oligonucleotides that contain the gene-specific sequences containing a T7 RNA polymerase promoter and binding site and a sequence encoding the affinity tag. Alternatively, an adaptor protein can be fused to the gene of interest by PCR. Amplified DNAs can be directly transcribed and translated in the *Escherichia coli* lysates without prior cloning for fast analysis. The proteins are then isolated by binding to an affinity matrix and processed as described above.

Alternative systems which may be used include wheat germ extracts and reticulocyte extracts. In vitro synthesis of membrane proteins and or post-translationally modified proteins will require reticulocyte lysates in combination with microsomes.

The present invention also provides for methods of using the invention array. The arrays of the present invention are particularly suited for the use in high-throughput drug screening. Other uses include medical diagnostics and biosensors.

Use of one of the protein arrays of the present invention may optionally involve placing the two-dimensional protein array in a flowchamber with approximately 1–10 microliters of fluid volume per 25 mm$^2$ overall surface. The cover over the array in the flowchamber is preferably transparent or translucent. In one embodiment, the cover may comprise Pyrex or quartz glass. In other embodiments, the cover may be part of a detection system that monitors interaction between biological moieties immobilized on the array and an analyte. The flowchambers should remain filled with appropriate aqueous solutions to preserve protein activity. Substrates and potential drug compounds may be flushed into the flow chamber as desired and their interaction with the immobilized proteins determined. Hence, no specialized microfluidic pumps, valves, or mixing techniques are required for fluid delivery to the array.

In an alternative embodiment, fluid can be delivered to each of the patches of the array individually. For instance, in one embodiment, the regions of the substrate surface may be microfabricated in such a way as to allow integration of the array with a number of fluid delivery channels oriented perpendicular to the array surface, each one of the delivery channels terminating at the site of an individual protein-coated patch.

Possible interactions towards which the present invention may be directed include, but are not limited to, antibody/antigen, antibody/hapten, enzyme/substrate, carrier protein/substrate, lectin/carbohydrate, receptor/hormone, receptor/effector, protein/DNA, protein/RNA, repressor/inducer, or the like.

A method for screening a plurality of proteins for their ability to interact with a component of a fluid sample comprises delivering the fluid sample to the invention array, and detecting the interaction of said component with the immobilized protein of each patch.

A wide range of detection methods is applicable to this and other methods of the invention. The invention device can be interfaced with optical detection methods such as absorption in the visible range, chemoluminescence, and fluorescence (including lifetime, polarization, fluorescence correlation spectroscopy (FCS), and fluorescence-resonance energy transfer (FRET)). Furthermore, built-in detectors such as optical waveguides PCT Publication WO 96/26432 and U.S. Pat. No. 5,677,196, surface plasmons, and surface charge sensors are compatible with many embodiments of the invention.

Figure 9:
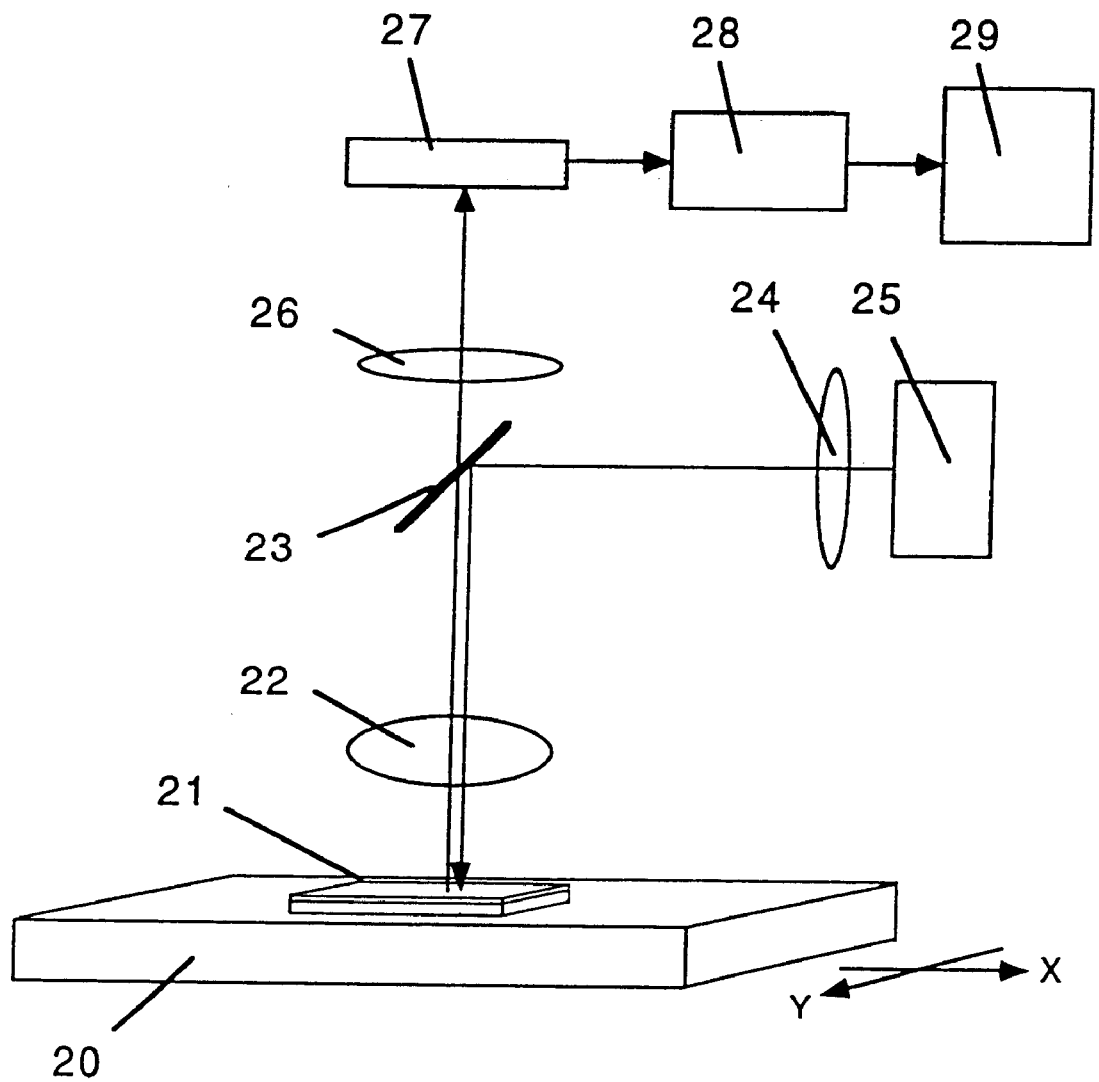
FIG. 9 shows a schematic of a fluorescence detection unit which may be used to monitor interaction of the proteins of the array with an analyte.

FIG. 9 shows a schematic diagram of one type of fluorescence detection unit which may be used to monitor interaction of immobilized proteins of an array with an analyte. In the illustrated detection unit, the protein array 21 is positioned on a base plate 20. Light from a 100 W mercury arc lamp 25 is directed through an excitation filter 24 and onto a beam splitter 23. The light is then directed through a lens 22, such as a Micro Nikkor 55 mm 1:2:8 lens, and onto the array 21. Fluorescence emission from the array returns through the lens 22 and the beam splitter 23. After next passing through an emission filter 26, the emission is received by a cooled CCD camera 27, such as the Slowscan TE/CCD-1024SF&SB (Princeton Instruments). The camera is operably connected to a CPU 28 which is in turn operably connected to a VCR/monitor 29.

Another aspect of the invention provides for a method for screening a plurality of proteins for their ability to bind a component of a fluid sample. This method comprises, delivering said fluid sample to the invention array, washing the array with fluid which does not contain said component in order to elute unbound component from the surface of the array, and detecting, either directly or indirectly, the presence, absence, or amount of the component retained at each patch.

Another embodiment of the invention provides a method for detecting in parallel the ability of a drug candidate to interfere with the ability of a singular analyte or a plurality of analytes in a fluid sample to bind one or more immobilized proteins on the invention array. This method comprises delivering the fluid sample to the invention array, washing said array with analyte free fluid to remove unbound analyte, and detecting, either directly or indirectly, the presence of analyte retained at each patch.

The array of the present invention may also be used in a diagnostic manner. In the diagnostic embodiments of the invention, the plurality of proteins immobilized on the array are not preferably members of the same protein family. One embodiment of the invention provides a method for detecting in parallel the presence of a plurality of analytes in a fluid sample which react with one or more of the immobilized proteins. This method comprises delivering the fluid sample to the invention array and detecting the interaction of the analyte with the immobilized protein at each patch.

A method for detecting in parallel the presence of a plurality of analytes in a fluid sample which bind said one or more of the immobilized proteins, comprises delivering the fluid sample to the invention array, washing said array with an analyte-free fluid to remove unbound analyte, and detecting, either directly or indirectly, the presence of analyte retained at each patch.

(c) Alternative Embodiments of Protein-coated Substrates.

Another embodiment of the present invention is a protein-coated substrate comprising the following: a substrate; a monolayer on a portion of a surface of the substrate that comprises molecules of the formula X-R-Y where R is a spacer, X is a functional group that binds R to the surface, and Y is a functional group for binding a fusion protein onto the monolayer; an affinity tag that enhances site-specific immobilization of the fusion protein onto the monolayer; and a fusion protein of a first polypeptide linked to a second, adaptor polypeptide, immobilized on said monolayer by means of the affinity tag that is linked to the second, adaptor polypeptide.

One of ordinary skill in the art will appreciate that numerous materials and compounds may be selected for the elements of the substrate, R, Y, X, the affinity tag, and the adaptor polypeptide of this embodiment.

The substrate may be organic or inorganic, biological or non-biological, or any combination of these materials. The substrate of the invention can optionally comprise a material selected from a group consisting of silicon, silica, quartz, glass, controlled pore glass, carbon, alumina, titanium dioxide, germanium silicon nitride, zeolites, and gallium arsenide. Many metals such as gold, platinum, aluminum, copper, titanium, and their alloys are also options for substrates. In addition, many ceramics and polymers may be used as substrates. Photoresists, polymerized Langmuir-Blodgett films, and LIGA structures may also serve as substrates in the present invention. The preferred substrates of the present invention comprise silicon, silica, glass, or a polymer.

In an alternative embodiment, the protein-coated substrate further comprises a coating between said substrate and said monolayer. This coating may be formed on the substrate or applied to the substrate. The coating on the substrate may comprise a metal film. In a preferred embodiment, the coating is a noble metal film. Many other different coatings, such as a polymer, glass, a hydroxylated surface, silicon nitride and silicon oxide are also compatible with the present invention.

In some embodiments of the invention, the protein-coated substrate will further comprise at least one adhesion layer or mediator between the coating and the substrate.

A variety of chemical moieties may function as monolayers in the array of the present invention. However, three major classes of monolayer formation are preferably used to expose high densities of bioreactive omega-functionalities on the patches of the array: (i) alkylsiloxane monolayers ("silanes") on hydroxylated surfaces (as taught in, for example, U.S. Pat. No. 5,405,766, PCT Publication WO 96/38726, U.S. Pat. Nos. 5,412,087, and 5,688,642); (ii) alkyl-thiol/dialkyldisulfide monolayers on noble metals (preferably Au(111)) (as, for example, described in Allara et al., U.S. Pat. No. 4,690,715; Bamdad et al., U.S. Pat. No. 5,620,850; Wagner et al., *Biophysical Journal*, 1996, 70:2052–2066); and (iii) alkyl monolayer formation on oxide-free passivated silicon (as taught in, for example, Linford et al., *J. Am. Chem. Soc.*, 1995, 117:3145–3155, Wagner et al., *Journal of Structural Biology*, 1997, 119:189–201, U.S. Pat. No. 5,429,708). One of ordinary skill in the art, however, will recognize that many possible moieties may be substituted for X, R, and/or Y, dependent primarily upon the choice of substrate, coating and affinity tag.

R of a monolayer molecule may comprise a hydrocarbon chain from about 1 to about 200 carbons long. The hydrocarbon chain may comprise an alkyl, aryl, alkenyl, alkynyl, cycloalkyl, alkaryl, aralkyl group, or any combination thereof. In a preferred embodiment, R is an alkane from about 8 to about 22 carbons long. However, it is also contemplated that in an alternative embodiment, R may readily comprise a hydrocarbon chain from about 2 to about 200 carbons long and interrupted by at least one hetero atom.

X may be chosen as any group which affords chemisorption or physisorption of the monolayer onto the surface of the substrate (or the coating, if present). For instance, especially if the substrate or coating is a metal or metal alloy, x at least prior to incorporation into the monolayer, may be chosen to be an asymmetrical or symmetrical disulfide, sulfide, diselenide, selenide, thiol, isonitrile, selenol, trivalent phosphorus compounds, isothiocyanate, isocyanate, xanthanate, thiocarbamate, phosphines, amines, thio acid and dithio acid. This embodiment is especially preferred when a coating or substrate is used that is a noble metal such as gold, silver, or platinum.

In alternative embodiments, X prior to incorporation into the monolayer, may be a hydroxyl, carboxyl, vinyl, sulfonyl, phosphoryl, silicon hydride, or an amino group. Another possibility is that prior to incorporation into the monolayer, X can be a free-radical-producing moiety.

If the substrate of the protein-coated substrate is a material such as silicon, silicon oxide, indium tin oxide, magnesium oxide, alumina, quartz, glass, or silica, then a preferred embodiment of the invention comprises an X that, prior to incorporation into said monolayer, is a monohalosilane, dihalosilane, trihalosilane, trialkoxysilane, dialkoxysilane, or a monoalkoxysilane. In preferred embodiments, the silane is a trichlorosilane or trialkoxysilane.

The component, Y, of the monolayer is responsible for binding a biological moiety onto the monolayer. In a preferred embodiment of the invention, the Y group is either highly reactive (activated) towards the biological moiety or is easily converted into such an activated form. In a preferred embodiment, the coupling of Y with the biological moiety occurs readily under physiological conditions.

In one embodiment of the present invention, Y is a functional group that is activated in situ. Possibilities for this type of functional group include, but are not limited to, such simple moieties such as a hydroxyl, carboxyl, amino, aldehyde, carbonyl, methyl, methylene, alkene, alkyne, carbonate, aryliodide, or a vinyl group. Alternatively, Y can comprise a functional group that requires photoactivation prior to becoming activated enough to trap the biological moiety.

In an especially preferred embodiment of the protein-coated substrate of the present invention, Y is a highly reactive functional moiety. Such possibilities for Y include, but are not limited to, maleimide, N-hydroxysuccinimide, nitrilotriacetic acid, activated hydroxyl, haloacetyl, bromoacetyl, iodoacetyl, activated carboxyl, hydrazide, epoxy, aziridine, trifluoromethyldiaziridine, pyridyldisulfide, N-acyl-imidazole, imidazolecarbamate, succinimidylcarbonate, arylazide, anhydride, diazoacetate, benzophenone, isothiocyanate, isocyanate, imidoester, fluorobenzene, and biotin.

The monolayer of the protein-coated substrate can optionally comprise at least two different X-R-Y molecules. Alternatively, the monolayer can further comprise a second molecule that is of the formula X-R-V wherein R is a spacer, X is a functional group that binds R to the surface, and V is a moiety resistant to the non-specific binding of polypeptides and proteins.

In one embodiment of the protein-coated substrate, the affinity tag is a polypeptide or an amino acid. In a preferred embodiment of the protein-coated substrate, the affinity tag comprises a poly(amino acid). Amino acid tags provide either a single amino acid or a series of amino acids that can interact with the Y-functionalities of the monolayer. Amino acid affinity tags can also be introduced to a specific site on a recombinant protein to facilitate oriented immobilization by covalent binding to the bioreactive Y-functional group of the monolayer.

The affinity tag may comprise a poly(amino acid) tag. A poly(amino acid) tag is a polypeptide that comprises from about 2 to about 100 residues of a single amino acid. For instance, the affinity tag may comprise a poly-cysteine, poly-lysine, poly-arginine, or poly-histidine. Amino acid tags are preferably composed of two to twenty residues of a single amino acid, such as, for example, histidines, lysines, arginines, cysteines, glutamines, tyrosines, or any combination of these. According to a preferred embodiment, an amino acid tag of one to twenty amino acids includes at least one to ten cysteines for thioether linkage; or one to ten lysines for amide linkage; or one to ten arginines for coupling to vicinal dicarbonyl groups. One of ordinary skill in the art can readily pair suitable affinity tags with a given Y-functional group.

The position of the amino acid tag can be at the amino-, or carboxy-terminus of the protein or anywhere in between. Where compatible with protein function, affinity tags introduced for protein purification are preferentially located at the C-terminus of the recombinant protein to ensure that only full-length proteins are isolated during protein purification.

Affinity tags may also contain one or more unnatural amino acids. Unnatural amino acids can be introduced using suppressor tRNAs that recognize stop codons (i.e. amber). The tRNAs are chemically amino-acylated to contain chemically altered ("unnatural") amino acids for use with specific coupling chemistries (i.e. ketone modifications, photoreactive groups).

In an alternative embodiment the affinity tag can comprise a whole protein, such as, but not limited to, glutathione S-transferase, an antibody, avidin, or streptavidin.

Other protein conjugation and immobilization techniques known in the art may be adapted for the purpose of immobilizing proteins on activated monolayers. For instance, an organic bioconjugate, such as biotin or an antigen, amy be chemically cross linked to the protein to be immobilized.

In a preferred embodiment, the fusion protein that comprises the first and second polypeptides comprises the affinity tag as well. Methods for the expression of fusion proteins have been outlined above.

In one embodiment of the protein-coated substrate, the adaptor polypeptide is protein G or protein A. Adaptor proteins are especially useful to increase the solubility of the protein of interest and to increase the distance between the surface of the substrate or coating and the protein of interest. Use of an adaptor protein or polypeptide can also be very useful in facilitating the preparative steps of protein purification by affinity binding. Examples of possible adaptor proteins include glutathione-S-transferase (GST), maltose-binding protein, chitin-binding protein, thioredoxin, green-fluorescent protein (GFP). GFP can also be used for quantification of surface binding.

(d) EXAMPLES

The following specific examples are intended to illustrate the invention and should not be construed as limiting the scope of the claims:

Example 1

Fabrication of a Two-dimensional Array by Photolithography

In a preferred embodiment of the invention, two-dimensional arrays are fabricated onto the device material via standard microstereolithography and/or thin film deposition. Alternative techniques include microcontact printing. Usually, a computer-aided design pattern (reflecting the final channel geometries) is transferred to a photomask using standard techniques, which is then used to transfer the pattern onto a silicon wafer coated with photoresist.

In a typical example, the device ("chip") with lateral dimensions of 20×20 mm contains an array of squared patches of a bioreactive layer (here: gold on silicon) each 0.1×0.1 mm in size and separated by hydrophobic surface areas with a 0.2 mm spacing. 4" diameter Si(100) wafers (Virginia Semiconductor) or 4" diameter Corning 7740 glass wafers are used as bulk materials. Si(100) wafers are first cleaned in a 5:1:1 deionized (DI) water:$NH_3$:$H_2O_2$ bath (RCA1, 90° C., 10 min), followed by a 5:1:1 DI water:HCl:$H_2O_2$ bath (RCA2, 90° C., 10 min) and finally passivated in 1% aqueous HF and singed at 150° C. for 30 min to become hydrophobic. The wafer is then spincoated with photoresist (Shipley 1813), prebaked for 25 minutes at 90° C., exposed using a Karl Suss contact printer and developed according to standard protocols. The wafer is then dried and postbaked at 110° C. for 25 min. In the next step, the wafer is primed with a 20 nm thin titanium layer, followed by a 200 nm thin gold layer both layers deposited using electron-beam evaporation (5 Å/s, Thermionics). After resist stripping and a short plasma treatment, the gold patches can be further chemically modified to achieve the desired bioreactive and biocompatible properties (see Example 3, below).

Example 2

Fabrication of a Two-dimensional Array by Deposition Through a Hole Mask

In another preferred embodiment the array of gold patches is fabricated by thin film deposition through a hole mask which is in direct contact with the substrate. In a typical example, Si(100) wafers are first cleaned in a 5:1:1 deionized (DI) water : $NH_3$:$H_2O_2$ bath (RCA1, 90° C., 10 min), followed by a 5:1:1 DI water:HCl:$H_2O_2$ bath (RCA2, 90° C., 10 min) and finally passivated in 1% aqueous HF and singed at 150° C. for 30 min to become hydrophobic. The wafer is then brought into contact with a hole mask exhibiting the positive pattern of the desired patch array. In the next step, the wafer is primed with 20 nm thin titanium layer, followed by a 200 nm thin gold layer both layers deposited using electron-beam evaporation (5 Å/s, Thermionics). After removal of the mask, the gold patches can be further chemically modified to achieve the desired bioreactive and biocompatible properties (see Example 3, below).

Example 3

Synthesis of an Aminoreactive Monolayer Molecule (Following the Procedure Outlined in Wagner et al., *Biophys. J.*, 1996, 70:2052–2066)

General. $^1$H- and $^{13}$C-NMR spectra are recorded on Bruker instruments (100 to 400 MHz). Chemical shifts (δ) are reported in ppm relative to internal standard (($CH_3)_4$Si, δ=0.00 ($^1$H- and $^{13}$C-NMR)). FAB-mass spectra are recorded on a VG-SABSEQ instrument ($Cs^+$, 20 keV). Transmission infrared spectra are obtained as dispersions in KBr on an FTIR Perkin-Elmer 1600 Series instrument. Thin-layer chromatography (TLC) is performed on pre-coated silica gel 60 F254 plates (MERCK, Darmstadt, FRG), and detection was done using $Cl_2$/toluidine, $PdCl_2$ and UV-detection under $NH_3$-vapor. Medium pressure liquid chromatography (MPLC) is performed on a Labomatic MD-80 (LABOMATIC INSTR. AG, Allschwil, Switzerland) using a Buechi column (460×36 mm; BUECHI, Flawil, Switzerland), filled with silica gel 60 (particle size 15–40 μm) from Merck.

Synthesis of 11,11'-dithiobis(succinimidylundecanoate) (DSU). Sodium thiosulfate (55.3 g, 350 mmol) is added to a suspension of 11-bromo-undecanoic acid (92.8 g, 350 mmol) in 50% aqueous 1,4-dioxane (1000 ml). The mixture is heated at reflux (90° C.) for 2 h until the reaction to the intermediate Bunte salt was complete (clear solution). The oxidation to the corresponding disulfide is carried out in situ by adding iodine in portions until the solution retained with a yellow to brown colour. The surplus of iodine is retitrated with 15% sodium pyrosulfite in water. After removal of 1,4-dioxane by rotary evaporation the creamy suspension is filtered to yield product 11,11'-dithiobis(undecanoic acid). Recrystallization from ethyl acetate/THF provides a white solid (73.4 g, 96.5%): mp 94° C.; $^1$H NMR (400 MHz, CDCl$_3$/CD$_3$OD 95:5): δ2.69 (t, 2H, J=7.3 Hz), 2.29 (t, 2H, J=7.5 Hz), 1.76–1.57 (m, 4H), and 1.40–1.29 (m, 12H); FAB-MS (Cs$^+$, 20 keV): m/z (relative intensity) 434 (100, M$^+$). Anal. Calcd. for C$_{22}$H$_{42}$O$_4$S$_2$: C, 60.79; H, 9.74; S, 14.75. Found: C, 60.95; H, 9.82; S, 14.74. To a solution of 11,11'-dithiobis(undecanoic acid). (1.0 g, 2.3 mmol) in THF (50 ml) is added N-hydroxysuccinimide (0.575 g, 5 mmol) followed by DCC (1.03 g, 5 mmol) at 0° C. After the reaction mixture is allowed to warm to 23° C. and is stirred for 36 h at room temperature, the dicyclohexylurea (DCU) is filtered. Removal of the solvent under reduced pressure and recrystallization from acetone/hexane provides 11,11'-dithiobis(succinimidylundecanoate) as a white solid. Final purification is achieved by medium pressure liquid chromatography (9 bar) using silica gel and a 2:1 mixture of ethyl acetate and hexane. The organic phase is concentrated and dried in vacuum to afford 11,11'-dithiobis (succinimidylundecanoate) (1.12 g, 78 %): mp 95° C.; $^1$H NMR (400 MHz, CDCl$_3$): δ2.83 (s, 4H), 2.68 (t, 2H, J=7.3 Hz), 2.60 (t, 2H, J=7.5 Hz), 1.78–1.63 (m, 4H), and 1.43–1.29 (m, 12H); FAB-MS (Cs$^+$, 20 keV): m/z (relative intensity) 514 (100), 628 (86, M$^+$). Anal. Calcd. for C$_{30}$H$_{48}$N$_2$O$_8$S$_2$: C, 57.30; H, 7.69; N, 4.45; S, 10.20. Found: C, 57.32; H, 7.60; N, 4.39; S, 10.25.

Example 4

Formation of an Aminoreactive Monolayer on Gold (Following the Procedure of Wagner et al., *Biophys. J.*, 1996, 70:2052–2066)

Monolayers based on 11,11'-dithiobis (succinimidylundecanoate) (DSU) can be deposited on Au(111) surfaces of microdevices described under Examples 1 and 2 by immersing them into a 1 mM solution of DSU in chloroform at room temperature for 1 hour. After rinsing with 10 volumes of solvent, the N-hydroxysuccinimide-terminated monolayer is dried under a stream of nitrogen and immediately used for protein immobilization.

Example 5

Expression and Purification of Human Caspase Fusion Proteins

Caspases are cysteine proteases of the papain superfamily, with a different active site and catalytic mechanism than observed for papain, Wilson, K. P. et al., *Nature*, 1994 370:270–275. Caspases are important enzymes in the promotion of the cell death pathways and inflammation, Villa, et al., *TIBS*, 1997, 22:288–392. Identification of selective caspase inhibitors is essential to prevent cross-inhibition of other caspase-dependent pathways. Caspases 1, 2, 3, 4, 5, 6, 7, 8, 9, 10, Villa, et al., *TIBS*, 1997, 22:288–392 and new caspase homologs identified by the human genome project are PCR amplified and cloned into an *E. coli* expression vector containing an N-terminal histidine tag, Hochuli, et al., *Biotechnoloy,* 1988 6: 1321, a factor Xa cleavage site, a lysine tag and a tri-glycine linker. Fusion proteins are expressed, purified by nickel-nitrilotriacetic acid (NTA) agarose chromatography, the histidine tag removed by factor Xa cleavage, followed by gel filtration. Caspases are snap-frozen and stored in 20 mM PIPES, pH 7.2, 150 mM NaCl, 0.1% CHAPS, 10% sucrose at −80° C.

Example 6

Immobilization of Fusion Proteins on a 2D-protein Array

Caspase-fusion proteins can be immobilized to the aminoreactive monolayer surface of the bioreactive patches of the two-dimensional array (see Examples 1, 2, and 4 above). Caspase fusion proteins can be diluted to concentrations of 1 µg/ml in 20 mM PIPES, pH 7.2, 150 mM NaCl, 0.1% CHAPS, 10% sucrose and applied onto the bioreactive patches using a computer-aided, capillary-based dispensing system. After an immobilization period of 30 min, the 2D array was rinsed and subjected to analysis. Ultrapure water with a resistance of 18 MΩcm is generally useable for all aqueous buffers (purified by passage through a Barnstead Nanopure® system).

Example 7

Assay of Caspase Activity on a Two-dimensional Array

Caspase activity can be determined by a binding assay using three fluorescently labeled peptide aldehyde inhibitors that form a reversible thiohemiacetal moiety with the active site cysteine, Thornberry, *Methods in Enzymology,* 1994, 244:615–631. The peptides are adapted to caspase 1, 3, 4, 7: Dns (dansyl)-SS- DEVD-CHO, caspase 1: Dns-SS-VDVAD-CHO, caspase 6: Dns-SS-VQID-CHO, Talanian,*J. Biol. Chem.,* 1997, 272:9677–9682. The affinity for Ac-DEVD-CHO to caspase 1 is determined to be in the low nanomolar range, Thornberry, *Methods in Enzymology,* 1994, 244:615–631. The assay buffer is 20 mM PIPES, pH 7.2, 150 mM NaCl, 0.1% CHAPS, 10% sucrose, Stennicke, and Salvesen,*J. Biol Chem.,* 1997, 272:25719–25723. Fluorescently labeled peptides are mixed to a final concentration of 1 to 5 nM each, the potential drug compound added and flushed onto the 2D array. Peptides are allowed to bind for 10–60 min., unbound peptide removed by washing with buffer and the fluorescence intensity measured (excitation at 360 nm, emission at 470 nm).

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for screening a plurality of proteins for interactions with one or more components of a fluid sample comprising the steps of:

providing a substrate having a surface and an array of spaced-apart protein immobilization regions over said surface, said protein immobilization regions being effective to immobilize one or more selected proteins, and one or more border regions surrounding each protein immobilization region and separating such protein immobilization regions from one another, said border regions each comprising (i) an ordered hydrophobic monolayer formed of alkyl chains having proximal ends being chemisorbed or physisorbed to said surface within said protein immobilization regions, and opposite hydrophobic distal ends, (ii) a hydrophilic monolayer attached to said hydrophobic monolayer, said hydrophilic monolayer comprising hydrophilic chains, each hydrophilic chain having a proximal end by which said hydrophilic chain is linked to an alkyl chain distal end, and an opposite hydrophilic distal end, together said hydrophobic monolayer and hydrophilic monolayers forming said border regions effectively resistant to non-specific protein binding;

applying said selected proteins to said protein immobilization regions to form an array of protein regions having one or more selected proteins displayed within said protein immobilization regions such that each protein immobilization region is separated from other protein immobilization regions by border regions resistant to non-specific protein binding;

exposing said protein regions to said fluid sample; and, detecting said interaction(s), if any within said protein regions.

2. The method of claim 1, wherein said hydrophobic polymer chains are hydrocarbon chains of length 8–22 carbons.

3. The method of claim 1, wherein said hydrophilic polymer chains are polyethyleneglycol chains.

* * * * *